(12) United States Patent
Kim et al.

(10) Patent No.: US 7,307,544 B2
(45) Date of Patent: Dec. 11, 2007

(54) METHOD AND APPARATUS FOR COMMUNICATION BETWEEN INSIDE AND OUTSIDE OF TRANSMISSION MEDIUM USING TRANSMISSION MEDIUM AS COMMUNICATION LINE

(75) Inventors: Tae-Song Kim, Seoul (KR); Jong-Oh Park, Seoul (KR); Sung-Wook Moon, Namyangju (KR); Byung Kyu Kim, Seoul (KR); Kyung hwan Kim, Seoul (KR); Ji-Yoon Kang, Seoul (KR); Han Jung, Daejeon (KR)

(73) Assignee: Korea Institute of Science and Technology, Seoul (KR)

( * ) Notice: Subject to any disclaimer, the term of this patent is extended or adjusted under 35 U.S.C. 154(b) by 441 days.

(21) Appl. No.: 10/158,503

(22) Filed: May 30, 2002

(65) Prior Publication Data
US 2003/0092973 A1   May 15, 2003

(30) Foreign Application Priority Data
Nov. 14, 2001   (KR) ............................... 2001-70802

(51) Int. Cl.
*G08C 19/00* (2006.01)
(52) U.S. Cl. .................................. 340/870.07; 600/300
(58) Field of Classification Search ............. 340/573.1, 340/870.19; 375/134, 316, 340, 359, 360; 713/182; 380/265; 600/393, 508, 300; 607/32, 607/60, 61, 4; 708/313
See application file for complete search history.

(56) References Cited

U.S. PATENT DOCUMENTS

| | | | | |
|---|---|---|---|---|
| 4,987,897 A | * | 1/1991 | Funke | .......................... 607/32 |
| 5,546,422 A | * | 8/1996 | Yokev et al. | ................ 375/134 |
| 6,021,162 A | * | 2/2000 | Gaboury et al. | ............ 375/242 |
| 6,577,893 B1 | * | 6/2003 | Besson et al. | .............. 600/509 |
| 2002/0002371 A1 | * | 1/2002 | Acker et al. | ................... 606/27 |
| 2003/0009204 A1 | * | 1/2003 | Amundson et al. | ........... 607/60 |

OTHER PUBLICATIONS

Summary of New Energy and Industrial Technology Development Organization Entrusted R&D Report for FY 1995, Waseda University, dated Mar. 31, 1997.

(Continued)

*Primary Examiner*—Brian Zimmerman
*Assistant Examiner*—Hung Q Dang
(74) *Attorney, Agent, or Firm*—Scully, Scott, Murphy & Presser, P.C.

(57) ABSTRACT

A method for communication between inside and outside of a transmission medium using the transmission medium as a communication line, includes the steps of: receiving an electric signal having information related to a transmission medium from a plurality of sensors inside the transmission medium; conducting the electric signal to the transmission medium; and sensing the electric signal flowing to the outside of the transmission medium. Because a modulating unit is not necessary, a power consumption is minimized. In addition, since an electric signal is directly conducted to a medium, it is not necessary to use an antenna, and thus, degradation of a reception rate according to a directional property of the antenna can be prevented. Moreover, since the electric signal is directly generated in the medium and the medium is directly used as an electric conductor, the overall size of a transmitter is reduced.

29 Claims, 4 Drawing Sheets

OTHER PUBLICATIONS

A Study On The Wireless Biomedical Microsensing Systems, Waseda University, dated May 1996.
Application Of Advanced Technology To Medical Telemetry, Waseda University.
A Very Low-Power Consumption Wireless ECG Monitoring System Using Body As A Signal Transmission Medium, Waseda University.
Studies On Bio-Sensing Microsystems For Healthcare, Waseda University.
Studies On Multi-Micro Sensor For Microcapsule In Medical Use, Waseda University, dated Apr. 1997.
A Study On The Wireless Biomedical Microsensing Systems (The Second Report), Waseda University, dated Apr. 1997.

* cited by examiner

METHOD AND APPARATUS FOR COMMUNICATION BETWEEN INSIDE AND OUTSIDE OF TRANSMISSION MEDIUM USING TRANSMISSION MEDIUM AS COMMUNICATION LINE

BACKGROUND OF THE INVENTION

1. Field of the Invention

The present invention relates to a method and apparatus for communication between inside and outside of a transmission medium using the transmission medium as a communication line, and more particularly, to a method and apparatus for communication between inside and outside of a transmission medium using the transmission medium as a communication line in which a transmitter is placed inside a transmission medium and conducts an electric signal through the transmission medium to a receiver for receiving the electric signal, to thereby improve a reception rate of a signal without doing a damage to the transmission medium.

2. Description of the Background Art

A conventional communication method between inside and outside of a transmission medium is that if the transmission medium is a human body, information related to human body obtained by sensors in the internal organs of human body by using a radio frequency signal in a frequency domain harmless to men is transmitted outside the human body.

The conventional method, however, has problems that since a low speed data is modulated to the RF signal of a few to scores of MHz and transmitted, its power consumption is great.

In addition, due to the directional property problem of an antenna, the reception rate of the RF signal can be easily changed and it is not easy to have a compact size antenna and RF circuit.

SUMMARY OF THE INVENTION

Therefore, an object of the present invention is to provide a method and apparatus for communication between inside and outside of a transmission medium using the transmission medium as a communication line that are capable of minimizing a power consumption and having a compact size of overall size of a circuit without using an antenna, in which a signal including information on a transmission medium is transmitted from a sensor which is easily inserted into the inside of the transmission medium to obtain an image (for example, an image of a wall of bowel) of the inside of the transmission medium, to outside the transmission medium.

Another object of the present invention is to provide a method and apparatus for communication between inside and outside of a transmission medium using the transmission medium as a communication line, in which an electric signal is directly generated inside the transmission medium, the transmission medium is directly used as an electric conductor, an infinitesimal current flowing to the outside of the transmission medium is measured, a noise is removed from the measured electric signal to reproduce an original electric signal.

To achieve these and other advantages and in accordance with the purpose of the present invention, as embodied and broadly described herein, there is provided a method for communication between inside and outside of a transmission medium using the transmission medium as a communication line, including the steps of: receiving an electric signal having information related to a transmission medium from a plurality of sensors inside the transmission medium; conducting the electric signal to the transmission medium; and sensing the electric signal flowing to the outside of the transmission medium.

To achieve the above objects, there is further provided an apparatus for communication between inside and outside of a transmission medium using the transmission medium as a communication line, including: a transmitter for receiving an electric signal having information on a transmission medium from a plurality of sensors existing inside the transmission medium and conducting it to the transmission medium; and a receiver for sensing the electric signal flowing to the outside of the transmission medium.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
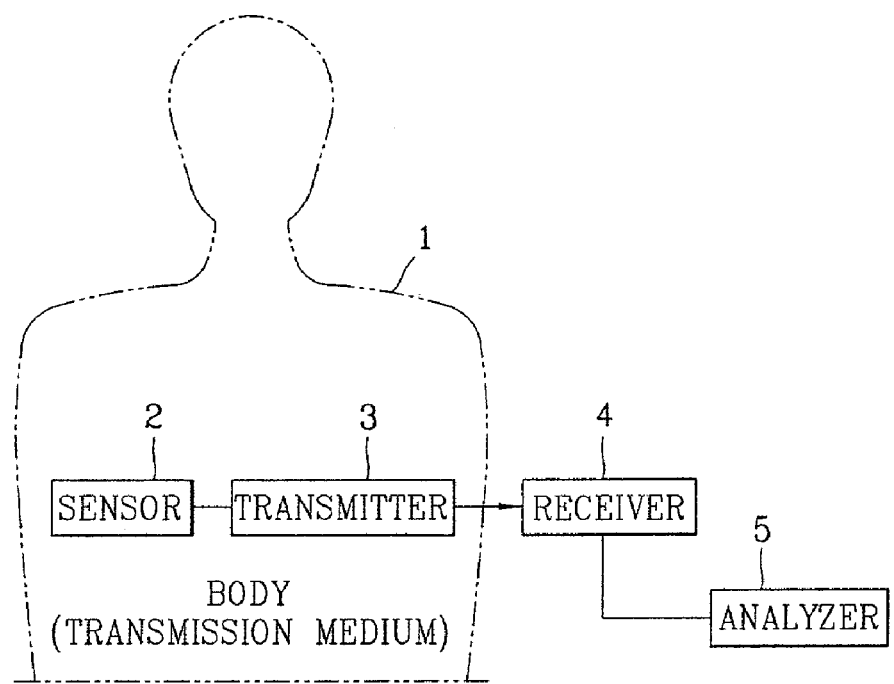
FIG. 1 is a schematic block diagram showing an apparatus for implementing a communication method in accordance with a preferred embodiment of the present invention.

FIG. 1 is a schematic block diagram showing an apparatus for implementing a communication method in accordance with a preferred embodiment of the present invention. In this case, the transmission medium is a human body.

As shown in FIG. 1, the apparatus for communication between inside and outside of a transmission medium using the transmission medium as a communication line includes: a human body 1; a sensor 2 positioned inside the human body 1 and collecting information on the human body 1; a transmitter 3 for receiving an electric signal of the sensor 2 and conducting the electrical signal through the human body 1; a receiver 4 for receiving the electric signal transmitted from the transmitter 3 through the human body 1; and an analyzer 5 for analyzing the signal received from the receiver 4.

Besides the human body, the transmission medium may include water and an aqueous solution with a chemical substance dissolved.

The information on the human body (or the medium) may be certain image information and sound information, or a result of substance analysis on a medium.

Figure 2:
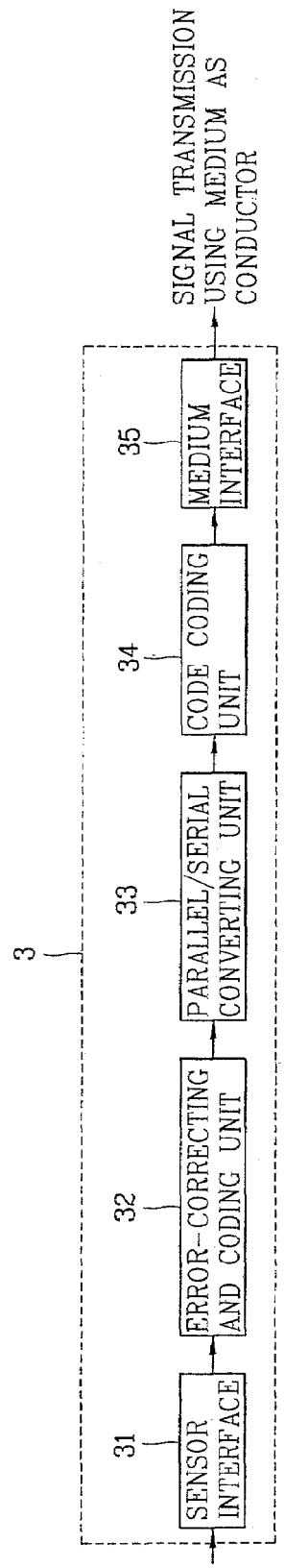
FIG. 2 is a schematic block diagram of a transmitter of FIG. 1 in accordance with the preferred embodiment of the present invention.

FIG. 2 is a schematic block diagram of a transmitter of FIG. 1 in accordance with the preferred embodiment of the present invention.

As shown in FIG. 2, the transmitter of FIG. 1 includes: a sensor interface 31 for receiving the electric signal of the sensor 2; an error correction coding unit 32 for adding a surplus bit (or data) to the inputted electric signal in order to improve a reliability; a parallel/serial converting unit 33 for converting the coded electric signal (generally, a parallel signal) into a serial signal; a code coding unit 34 (for example, a Manchester coding or a differential binary phase shift keying (DBPSK) coding) for converting the electric signal which has been converted into the serial signal into a certain code; and a human body (or medium) interface 35 for directly conducting the coded electric signal to the human body 1 (i.e., an inner wall of gastrointestines, etc.).

Rather than having a modulating unit as in the conventional art, the transmitter 3 conducts a base band as it is to the human body 1, so that it can transmit a signal at a speed of more than 1 MHz (or up to 2 to 3 Mhz).

Figure 3:
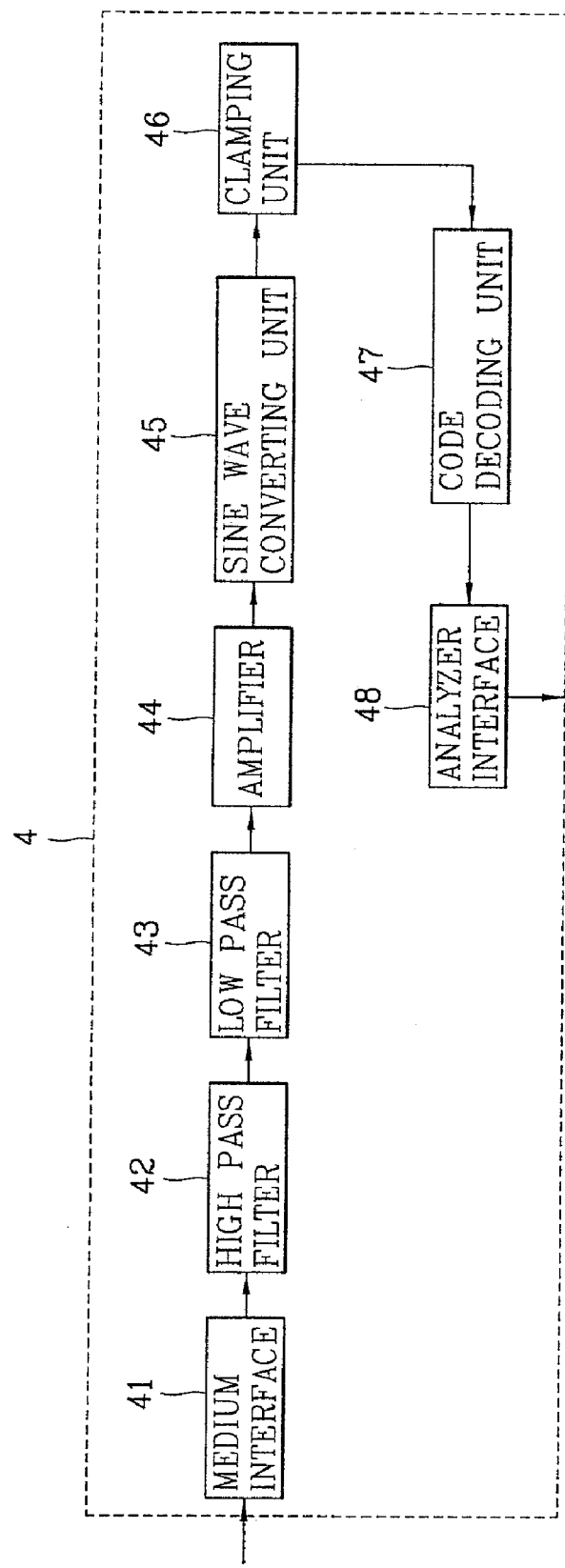
FIG. 3 is a schematic block diagram of a receiver of FIG. 1 in accordance with the preferred embodiment of the present invention.

FIG. 3 is a schematic block diagram of a receiver of FIG. 1 in accordance with the preferred embodiment of the present invention.

As shown in FIG. 3, the receiver of FIG. 1 includes a human body (or a medium) interface 41 contacting the human body 1 to receive the electric signal; a high pass filter 42 for filtering the received electric signal to remove a 60 Hz low frequency and high voltage noise; a low-pass filter 43 for filtering the electric signal to remove a high frequency noise; an amplifier 44 for amplifying the electric signal; a sine wave converting unit 45 for converting the amplified electric signal into a sine wave; a clamping unit 46 for converting the sine wave to a signal of transistor-transistor logic (TTL) level; a code decoding unit 47 for decoding the signal; and an analyzer interface 48 for transmitting the decoded signal to the analyzer 5.

In order to search only an edge of the electric signal, the high pass filter 42 uses a frequency of about one-half of the frequency of the received electric signal as a cut-off frequency.

In order to precisely restore the edge of the electric signal, the low pass filter 43 uses a frequency of 10 times as fast as the frequency of the received electric signal as a cut-off frequency.

The high pass filter 42 and the low pass filter may be comprehensively a noise removal filter 49.

The amplifier 44 amplifies the electric signal so that the sine wave converting unit 45 at the rear stage can be effectively operated.

The sine wave converting unit 45 generates a sine wave signal of a certain 2-step voltage (i.e., +/−12 volt) by detecting the edge component of the electric signal.

The sine wave converting unit 45 may be a Schmitt trigger circuit, and in such a case, the amplifier 44 is designed as a falling gain amplifier.

The clamping unit 47 converts the sine wave signal to a signal of 5 volt/0 volt of the TTL level.

The code decoding unit 47 decodes the received electric signal which has been coded.

The analyzer 5 may be, for example, a computer.

Figure 4:
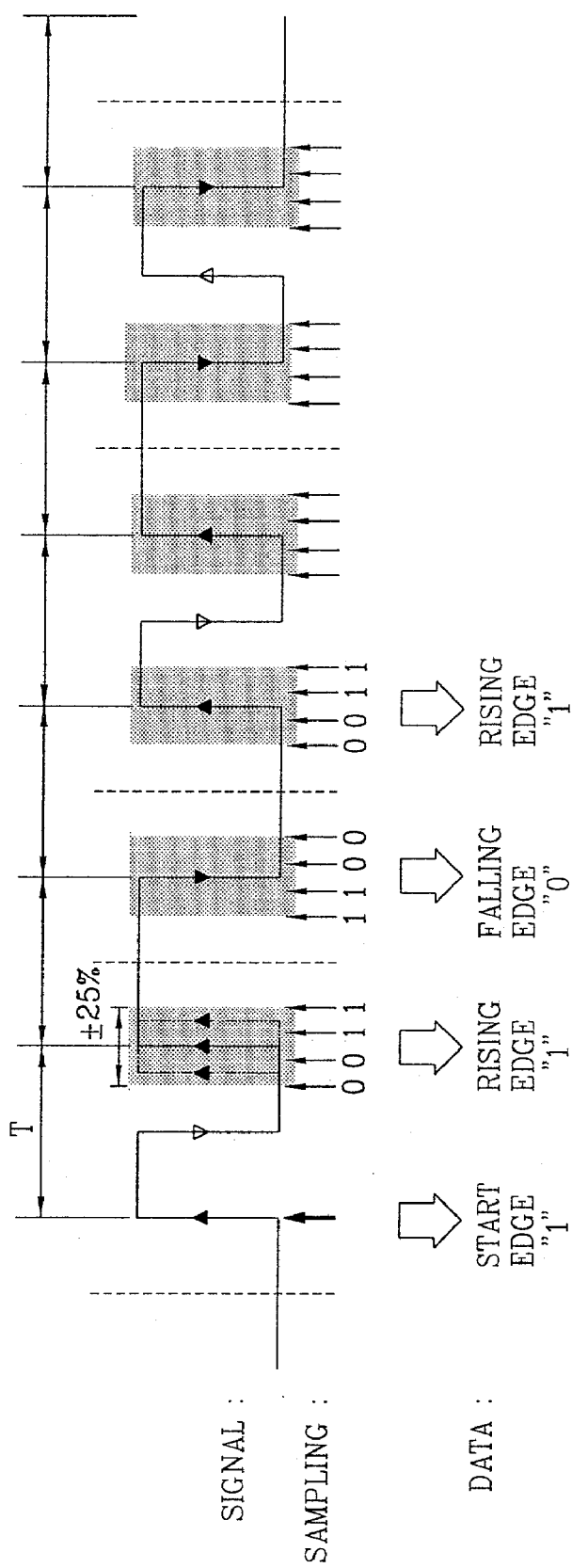
FIG. 4 is a graph showing a decoding method performed by a Manchester code decoding unit of FIG. 3 in accordance with the preferred embodiment of the present invention.

FIG. 4 is a graph showing a decoding method performed by a Manchester code decoding unit of FIG. 3 in accordance with the preferred embodiment of the present invention.

As shown in FIG. 4, a first rising edge (or an initiation edge) received by the code decoding unit 47 is designated as a data '1', and on the basis of the first rising edge, a rising edge or a falling edge is detected for every period (T) of the received electric signal, of which the rising edge is designated as a data '1' and the falling edge is designated as a data '0'.

Since the conversion edge (that is, a rising edge or a falling edge) of the electric signal is frequently generated within about ±25% of the period (T), a sampling is performed within about ±25% of the period (T) with a frequency of about 8 times faster than the frequency of the electric signal, to detect an electric signal.

As so far described, the method and apparatus for communication between inside and outside of a transmission medium using the transmission medium as a communication line of the present invention has many advantages.

That is, for example, first, because a modulating unit is not necessary, a power consumption is minimized.

Secondly, since an electric signal is directly conducted to a medium, it is not necessary to use an antenna, and thus, degradation of a reception rate according to a directional property of the antenna can be prevented.

Thirdly, since the electric signal is directly generated in the medium and the medium is directly used as an electric conductor, the overall size of a transmitter is reduced.

Lastly, since a carrier wave of a frequency like in the radio frequency communication method is not used in the present invention, so that the medium is not damaged.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the meets and bounds of the claims, or equivalence of such meets and bounds are therefore intended to be embraced by the appended claims.

What is claimed is:

1. A method for communication between inside and outside of a body using the body as a communication line, comprising the steps of:
   receiving an unmodulated baseband electric signal having information related to a body from a plurality of sensors inside the body;
   conducting the unmodulated baseband electric signal through the body in a frequency range from 1 MHz to 3 MHz; and
   sensing, from outside the body the unmodulated baseband electric signal flowing to the outside of the body.

2. The method of claim 1, further comprising the step of converting the unmodulated baseband electric signal into a serial signal, before the step of conducting the unmodulated baseband electric signal.

3. The method of claim 2, further comprising the step of coding the unmodulated baseband electric signal which has been converted into the serial signal, into a certain code.

4. The method of claim 3, wherein the certain code is a Manchester code.

5. The method of claim 3, wherein the certain code is a differential binary phase shift keying (DBPSK) code.

6. The method of one of claims 1, 2 or 3, further comprising the step of error-correcting and coding the unmodulated baseband electric signal, before the step of conducting the unmodulated baseband electric signal to the body.

7. The method of claim 1, wherein the step of sensing the unmodulated baseband electric signal comprises:
   converting the unmodulated baseband electric signal into a sine wave signal of two voltage levels; and clamping the unmodulated baseband electric signal which has been converted into to sine wave signal, into a signal of a logic level signal.

8. The method of claim 4 or 7, further comprising the step of decoding the unmodulated baseband electric signal which has been coded to a Manchester code.

9. The method of claim 5 or 7, further comprising the step of decoding the unmodulated baseband electric signal which has been coded to the DBPSK code.

10. The method of claim 8, wherein the step of decoding the coded unmodulated baseband electric signal comprises:
   detecting a first rising edge of the coded unmodulated baseband electric signal and designating the first rising edge as a data '1'; and
   detecting a rising or a falling edge for every signal period corresponding to a transmission frequency on the basis of the first rising edge and designating the rising edge or the falling edge as data '1' or '0'.

11. The method of claim 10, wherein the rising edge or the falling edge are detected with a faster frequency than the transmission frequency in a certain range of the transmission period.

12. The method of claim 11, wherein the certain range is about ±25% of the transmission period.

13. The method of claim 11, wherein the faster frequency is about 8 times of the transmission frequency.

14. The method of claim 1, wherein the step of sensing the unmodulated baseband electric signal comprises a step of removing a noise contained in the unmodulated baseband electric signal.

15. An apparatus for communication between inside and outside of a body using the body as a communication line, comprising:
   a transmitter located inside a body for receiving an unmodulated baseband electric signal having information on a body from a plurality of sensors existing inside the body and conducting the unmodulated baseband electric signal through the body in a frequency range from 1 MHz to 3 Mhz; and
   a receiver located outside a body for sensing the unmodulated baseband electric signal flowing to the outside of the body.

16. The apparatus of claim 15, wherein the transmitter includes a means for converting the unmodulated baseband electric signal into a serial signal.

17. The apparatus of claim 16, wherein the transmitter includes a means for coding the unmodulated baseband electric signal which has been converted into a serial signal, into a certain code.

18. The apparatus of claim 17, wherein the certain code is a Manchester code.

19. The apparatus of claim 17, wherein the certain code is a DBPSK code.

20. The apparatus of one of claims 15 to 17, the transmitter include a means for error-correcting and coding the unmodulated baseband electric signal.

21. The apparatus of claim 15, wherein the receiver comprises:
   a means for converting the unmodulated baseband electric signal into a sine wave signal of certain two voltage levels; and
   a clamping means for converting the unmodulated baseband electric signal which has been converted into the sine wave signal, into a logic level signal.

22. The apparatus of claim 18 or 21, wherein the receiver additionally comprises a means for decoding the unmodulated baseband electric signal which has been coded into a Manchester code.

23. The apparatus of claim 22, wherein, the means for decoding the coded unmodulated baseband electric signal detects a first rising edge of the coded electric signal to designated it as a data '1', and detects a rising edge or a falling edge for every signal period corresponding a transmission frequency on the basis of the first rising edge to designate it as '1' or '0'.

24. The apparatus of claim 23, wherein the rising or falling edge is detected with a faster frequency than the transmission frequency in a certain range of the transmission period.

25. The apparatus of claim 19 or 21, wherein the receiver additionally includes a means for decoding the unmodulated baseband electric signal which has been coded into the DBPSK code.

26. The apparatus of claim 15, wherein the receiver additionally includes a means for removing a noise contained in the unmodulated baseband electric signal.

27. The apparatus for communication of claim 15, wherein said receiver is placed in contact with the body to receive the unmodulated baseband electric signal.

28. A method for communication between inside and outside of a human body using the human body as a communication line, comprising the steps of:
   receiving an unmodulated baseband electric signal having information related to the human body from a plurality of sensors located inside the human body;
   conducting the unmodulated baseband electric signal converted into a certain code through the human body in a frequency range from 1 MHz to 3 MHz; and
   sensing the unmodulated baseband electric signal flowing to the outside of the human body.

29. The method of claim 28, wherein the certain code is a DBPSK code.

* * * * *